United States Patent [19]

Murtfeldt

[11] Patent Number: 4,957,484
[45] Date of Patent: Sep. 18, 1990

[54] LYMPH ACCESS CATHETERS AND METHODS OF ADMINISTRATION

[75] Inventor: Robert Murtfeldt, LaCanada, Calif.
[73] Assignee: Automedix Sciences, Inc., Torrance, Calif.
[21] Appl. No.: 224,395
[22] Filed: Jul. 26, 1988
[51] Int. Cl.⁵ .................. A61M 25/01; A61M 25/10
[52] U.S. Cl. ...................................... 604/53; 604/102; 604/164; 604/280
[58] Field of Search ............... 604/53, 93, 164, 102, 604/171, 170, 173, 264, 280; 128/657, 768–770

[56] References Cited

U.S. PATENT DOCUMENTS

| | | | |
|---|---|---|---|
| 3,690,323 | 9/1972 | Wortman et al. | 604/8 |
| 3,916,875 | 11/1975 | Toch | |
| 4,033,331 | 7/1977 | Guss et al. | 128/657 |
| 4,581,017 | 4/1986 | Sahota | 604/102 |
| 4,610,660 | 9/1986 | Rosenburg | 604/102 |
| 4,646,742 | 3/1987 | Packard et al. | |
| 4,692,139 | 9/1987 | Stiles | 604/108 |

Primary Examiner—Stephen C. Pellegrino
Attorney, Agent, or Firm—James E. Brunton

[57] ABSTRACT

A method and apparatus for accessing either the thoracic duct or the right lymphatic duct for removal of lymph fluids from the human body without the necessity of general surgery. The apparatus of the invention is provided with different forms of lymph fluid collection tips to enable collection of lymph fluid from patients whose lymph ducts terminate as single vessels as well as from patients whose lymph ducts terminate as many small vessels.

20 Claims, 4 Drawing Sheets

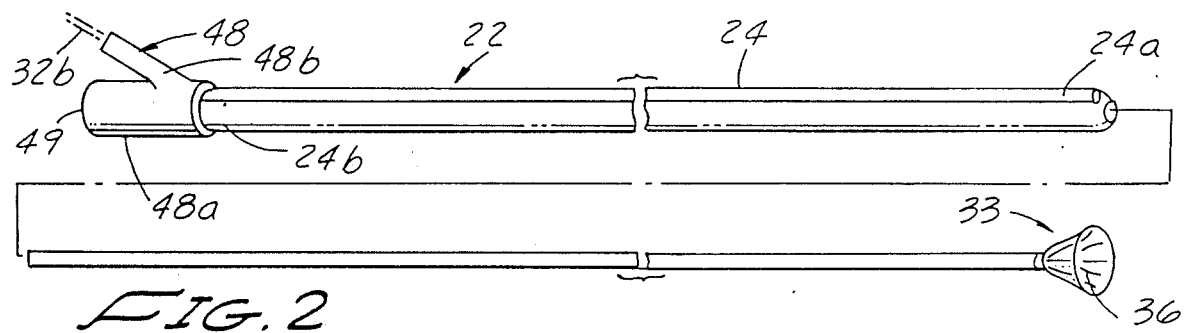
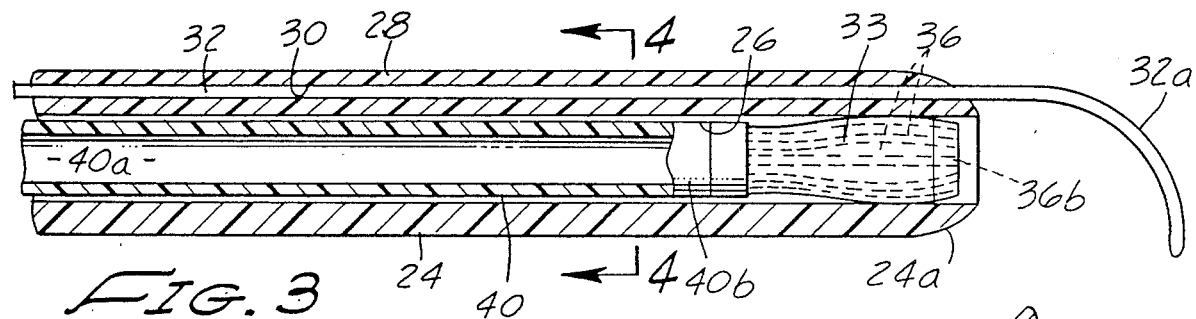
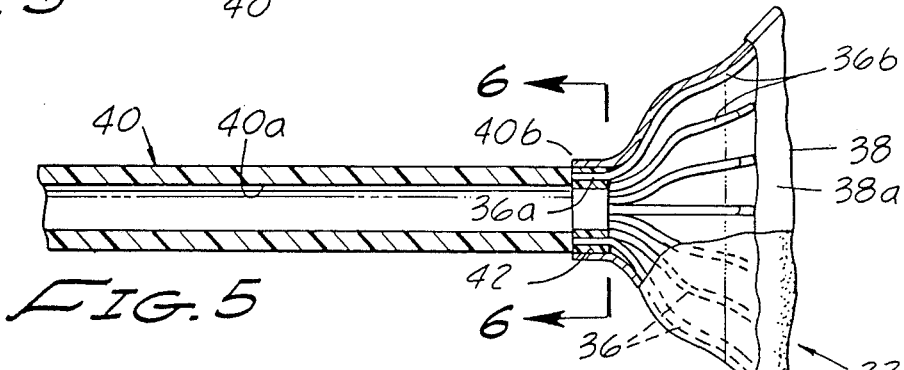
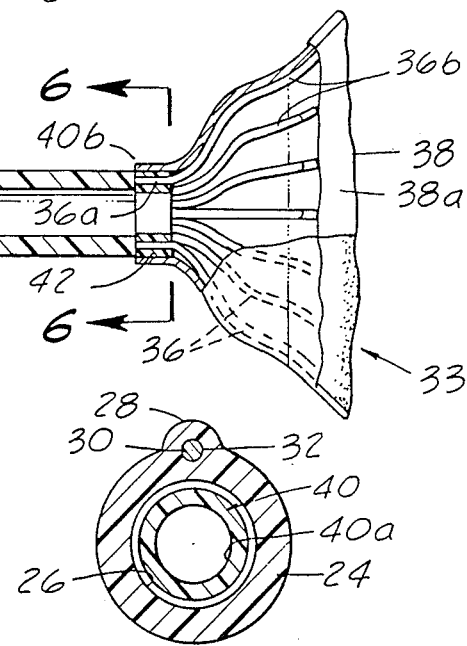
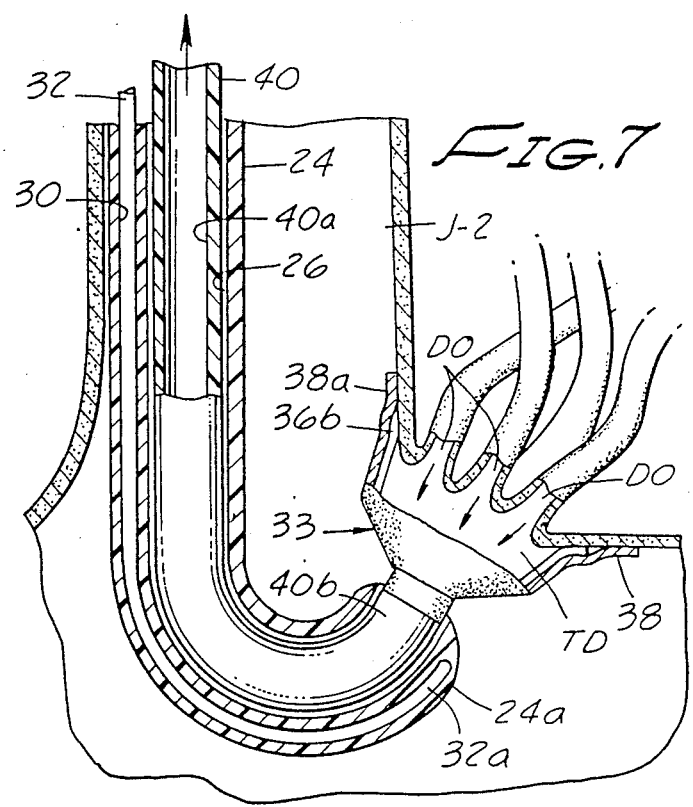
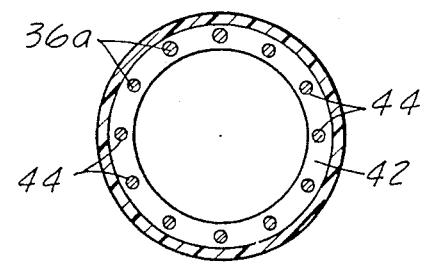

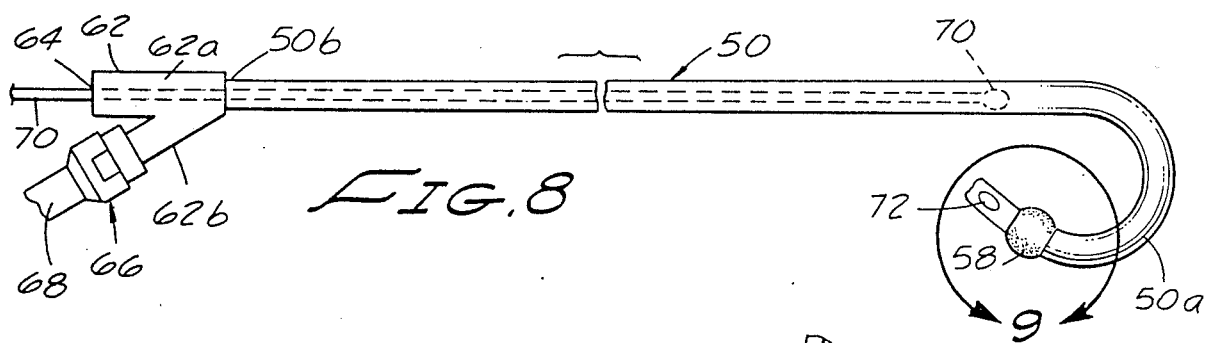
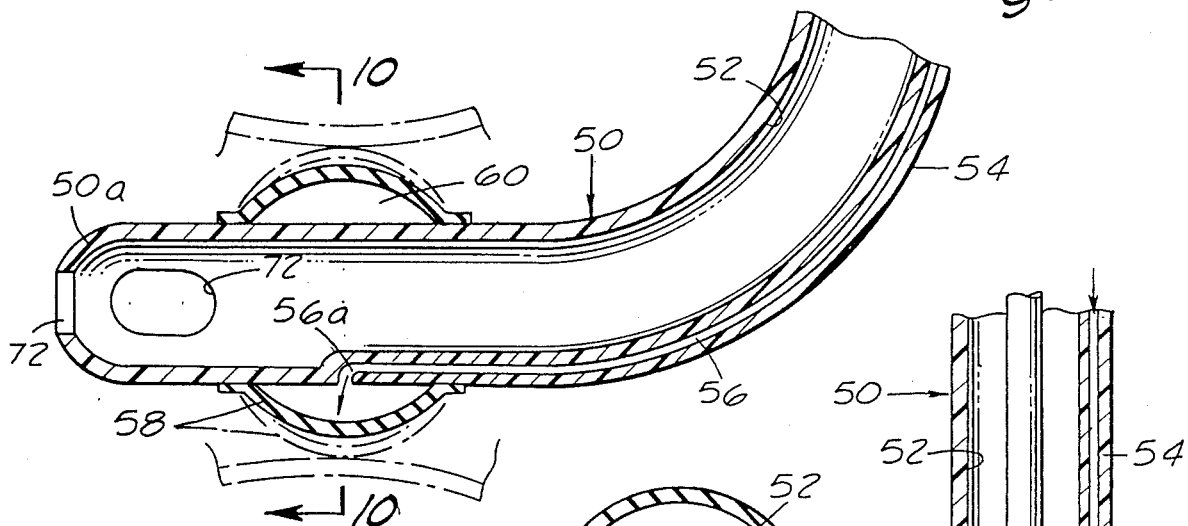
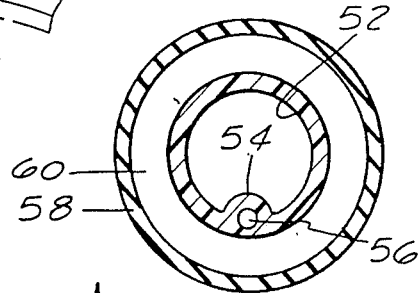
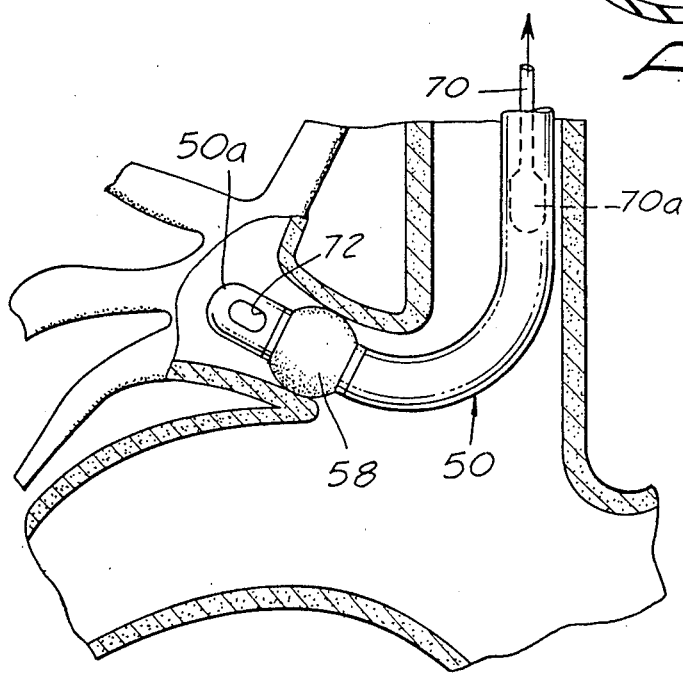
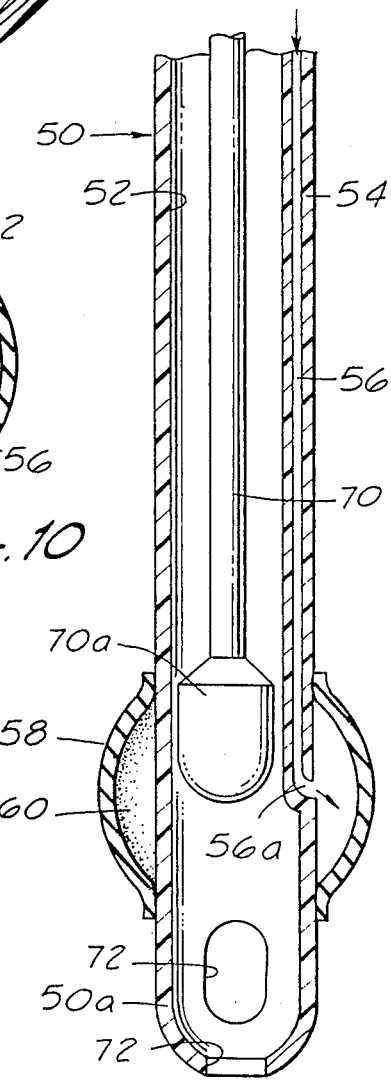

LYMPH ACCESS CATHETERS AND METHODS OF ADMINISTRATION

BACKGROUND OF THE INVENTION

1. Field of the Invention

The present invention relates to methods and apparatus for accessing the thoracic duct and the right lymphatic duct without general surgery for the purpose of collecting lymphatic white cells.

2. Discussion of the Prior Art

The majority of immune response physiology in humans is developed through white cells residing primarily in circulating blood, synovial fluid and lymph. In recognition of this fact, methods of extracting, treating and readministering these white cells, in particular T-cells, is continually gaining acceptance as a potentially effective modality for treating cancer, infections and autoimmune diseases. The current white cell extraction method of choice is leukopheresis of blood, in which a concentrated white cell solution is separated and extracted from whole blood.

While leukopheresis of blood has been an effective means of accessing and collecting white cells from blood, only about 7% of all white cells reside in blood at any one time. The wealth of circulating white cells contained in lymph fluid and in lymph nodes cannot be accessed by this method. Further, the majority of all circulating T-cells are found in lymph fluid and, therefore, cannot be accessed directly by leukopheresis of blood. The aforementioned drawbacks of present techniques for accessing white cells have limited the scope and efficacy of many white cell therapies.

Past efforts to access lymph fluid have involved general surgical procedures to cannulate the thoracic duct which transports approximately two-thirds of all lymph fluid into the bloodstream. In this procedure, the thoracic cavity is opened, the thoracic duct is severed from its junction with the left subclavian and internal jugular veins, and a cannula is sutured into the severed duct. Severe problems have developed in the majority of patients undergoing this procedure. Persistent cannulae-associated infections have developed which have required antibiotic therapy to control. In many cases, the thoracic duct has ruptured causing lymph fluid to leak into the thoracic cavity, requiring frequent lavage and drainage to control. Thoracic duct lymph leakage has also caused a general reduction in circulating T-cells and B-cells, which has resulted in symptoms of immune suppression. Also, frequent fibrin sheath formation around the tip of the cannulae has caused flow restriction and in some cases blockage of the cannulae. For these reasons, thoracic duct cannulation using general surgery has not been particularly acceptable to the medical community.

What has been urgently needed is an efficient method of accessing lymph fluid to obtain large quantities of white cells for white blood cell treatments, and one which avoids the high cost and severe complications associated with the thoracic surgery. Recent improvements in biomaterials have made it possible to conduct a central venous catheterization procedure to access the thoracic and right lymphatic ducts. This methodology together with the apparatus for accomplishing it forms the subject of the present invention.

SUMMARY OF THE INVENTION

It is an object of the present invention to provide methods and apparatus for accessing the thoracic and right lymphatic ducts without the use of general surgical procedures.

More particularly, it is an object of the invention to provide novel methods and apparatus for central venous catheterization to access the thoracic and right lymphatic ducts for the purpose of collecting lymph fluid.

Another object of the invention is to provide methods and apparatus of the aforementioned character in which the thoracic duct and tributaries are not directly affected and in which no ligation, cannulation or suturing is required.

Another object of the invention is to provide a unique catheter design for multilumen vascular access which can be effectively used to access lymph fluid in a higher percentage of candidates.

Another object of the invention is to provide a novel, dual lumen central venous catheter which includes a retractable cup-like assembly for fixation around several small ductile openings.

Still another object of the invention is to provide a catheter design of the character described in the proceeding paragraph in which catheter fixation is accomplished directly at the venous bifurcation by one of several alternate means.

Another object of the invention is to provide a catheter design which includes a balloon tip that can be inserted into the base of the thoracic duct and inflated with liquid or gas to retain the catheter securely in place.

Yet another object of the invention is to provide a catheter of the class described which can be easily removed when the treatment is completed.

A further object of the invention is to provide a catheter as described in the proceeding paragraphs which can be used to access both the thoracic and right lymphatic ducts.

Another object of the invention is to provide a catheter of the aforementioned character which is constructed from biocompatible materials and one which is easy and safe to use.

BRIEF DESCRIPTION OF THE DRAWINGS

FIG. 2 is a foreshortened, generally perspective view of one form of catheter of the present invention for use with patients whose lymph duct terminates in many small vessels not possible to access by internal catheterization.

FIG. 3 is a greatly enlarged cross-sectional view of the distal portion of the catheter illustrated in FIG. 2 showing the retractable vessel enclosure cup of the apparatus in a retracted configuration.

FIG. 4 is a cross-sectional view taken along lines 4—4 of FIG. 3.

FIG. 5 is a fragmentary cross-sectional view similar to FIG. 3 but showing the enclosure cup in an expanded configuration.

FIG. 6 is a cross-sectional view taken along lines 6—6 of FIG. 5.

FIG. 7 is a generally diagrammatic view illustrating the device of this form of invention in operative position with the enclosure cup surrounding the small vessels of the lymph duct.

FIG. 8 is a generally perspective view of an alternate form of catheter of the present invention for use with patients whose lymph ducts terminate as a single vessel.

FIG. 9 is an enlarged cross-sectional view of the distal portion of this form of the device indicated by the numeral 9 in FIG. 8.

FIG. 10 is a cross-sectional view taken along lines 10—10 of FIG. 9.

FIG. 11 is an enlarged cross-sectional view of the distal end of the device illustrated in FIG. 8 showing the guide wire in an extended position.

FIG. 12 is a generally diagrammatic view illustrating the device of this alternate form of the invention in position proximate the right lymphatic duct.

DESCRIPTION OF THE INVENTION

Figure 1:
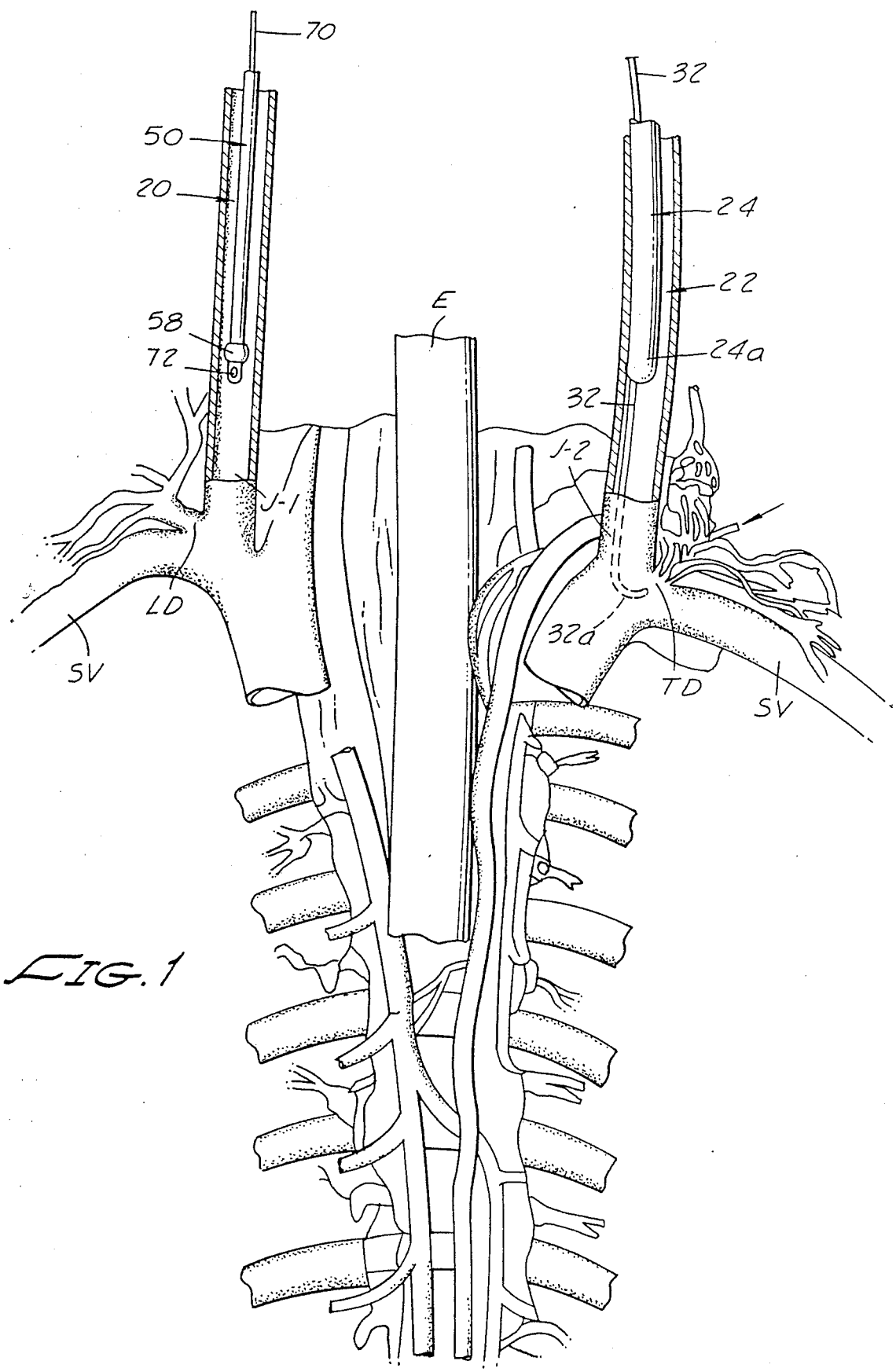
FIG. 1 is a generally diagrammatic view illustrating the location in the human body of the thoracic duct, the right lymphatic duct, the subclavian veins, the internal jugular veins and the esophagus and showing the manner by which the apparatus of the invention is used to access the thoracic duct and the right lymphatic duct.

Referring to the drawings, FIG. 1 diagrammatically illustrates the location within the human body of the thoracic duct, identified as "TD", and the right lymphatic duct, identified as "LD". The subclavian veins are identified in FIG. 1 a "SV" and the esophagus as "E".

The lymphatic system performs two important functions. First, the system contains lymph nodes which are sites for T-cell and B-cell maturation and expression, and important avenues for immune response. Second, the lymph system regulates interstitial tissue fluid levels and tissue perfusion rates. Circulating lymph fluid enters the lymph duct network as excess fluid, and is slowly drained into the blood stream through the thoracic and right lymphatic ducts. These two ducts are primary points for lymph system access and catheterization, since the ducts are the largest and most easily catheterized at this point. The thoracic duct terminates at the junction between the left internal jugular vein and the left subclavian vein. The right lymphatic duct terminates at the juncture between the right internal jugular and the right subclavian vein.

In approximately seventy percent of all patients, these lymph ducts terminate as single vessels and can be internally catheterized. For these patients, a balloon-type catheter is indicated for collecting lymph fluid. In the remaining patient group, the lymph ducts terminate as many small vessels, not possible to access by internal catheterization. For these patients, a special expander cup-type catheter is required. The uniquely designed expander cup device surrounds all the small vessels at the juncture for collecting lymph fluid.

The first mentioned form of the apparatus of the invention, which includes a balloon tip, is identified in FIG. 1 by the numeral 20 and is shown in position within the internal jugular vein J-1 at a location proximate the termination of the right lymphatic duct. An alternate form of the apparatus of the invention, namely the expander cup device, designated by the numeral 22, is shown in FIG. 1 in position within the internal jugular vein J-2. Both catheter designs made of silicone, latex, polyurethane, teflon, PVC or other materials, including any combinations or copolymers derived from these materials.

Considering first the expander cup form of the invention shown in greater detail in FIGS. 2 through 7, this embodiment of the invention comprises a three lumen catheter and includes an elongated tubular member 24 having first and second ends 24a and 24b respectively. As best seen by referring to FIG. 3 the elongated tubular member 24 includes an axially extending central passageway or lumen 26 and a wall portion 28 having a second lumen or passageway 30 extending longitudinally thereof.

A guide means provided here in the form of an elongated wire 32 having a curved end 32a is slidably receivable within second passageway 30 and functions to guide the first end of the apparatus into close proximity with lymph ducts which terminate as many small vessels or ductile openings, as for example, those illustrated in FIG. 7.

Forming an important aspect of the apparatus of the invention, is lymph fluid collection means which is located proximate the first end of tubular member 24 for collecting lymph fluid from lymph ducts of the character which terminate in a multiplicity of ductile openings. In the present embodiment of the invention, the lymph fluid collection means is provided in the form of an expander means of the character generally designated by the numeral 33 in FIGS. 5 and 7. Referring particularly to FIGS. 5 and 6, the expander means can be seen to comprise an expanding umbrella like apparatus movable between a first contracted position as shown in FIG. 3, wherein the expander assembly is disposed interiorly of the central passageway 26 of the tubular member 24, to a second expanded position as shown in FIG. 5 wherein the expander assembly is disposed exteriorly of the central passageway of the tubular member 24. The expander assembly, or lymph fluid collection means, is made up of a plurality of yieldably deformable tangs 36, made of stainless steel or rigid polymer or similar material, each having an outer end 36b and an inner end 36a. Carried proximate the outer ends of the tangs is a flexible sheath 38, made of sheet elastomer or hydrogel or similar material, which circumvents the tangs 36 and terminates in a circumferentially extending skirt portion or lip 38a (FIG. 5).

The inner end 36a of tangs 36 are connected to the first end 40b of a second elongated tubular member, or hollow stylus 40 which, as shown in FIG. 3, is slidably receivable within central passageway or lumen, 26 of tubular member 24. The central passageway 40a of member 40 comprises the third lumen of the catheter. As best seen by referring to FIG. 6, the first end 40b of second tubular member 40 is provided with a ring shaped member 42 having a plurality of circumferentially spaced apertures 44 which closely receive and securely support the inner ends 36a of tangs 36. The tangs 36 are pre-formed so that when the ends 36a thereof are held captive within apertures 44 in ring 42 the tang will bow outwardly in the general umbrella-like fashion illustrated in FIG. 5. In this expanded configuration, the outer ends of the tangs define a circle whose diameter is substantially larger than the diameter of lumen 26 formed in tubular member 24. The tangs are sufficiently yieldable so that when second tubular member 40 is withdrawn into tubular member 24 in the manner shown in FIG. 3 the tangs will fold together into their first retracted position shown in FIG. 3. However, when member 40 is slidably moved forwardly, that is, toward the first end of tubular member 24 each tang 36, because of its bow shaped memory, will expand outwardly in the fashion shown in FIG. 5. The flexible sheath 38 which surrounds the outer ends of tangs 36 is designed to neatly fold into the configuration shown in FIG. 3 when member 40 is withdrawn into the lumen of member 24.

Turning now particularly to FIGS. 1 and 7, in using the apparatus of the form of the invention described in the preceding paragraphs, the guide wire 32 is slidably positioned within elongated second passageway 30 in a manner such that the first end 32a thereof extends outwardly from member 24 a substantial distance. Provided at the second end of member 24 is a generally Y-shaped assemblage 48 having a body portion 48a one end of which is closely receivable over end 24b of tubular member 24. Provided at the other end of body portion 48a is a fluid drainage port 49. Extending angularly outwardly from body portion 48a is a tubular segment 48b which slidably receives guide wire 32.

In the starting position of the apparatus, end 32b of guide wire 32 extends outwardly from the apparatus through tubular section 48b of assemblage 48. Preferably, the catheter is radio-opaque, or includes a radio-opaque stripe to facilitate the use of fluoroscopy to confirm catheter location and orientation in a manner well known to those skilled in the art. With the apparatus in the described starting position, the guide wire 32 is carefully inserted into the jugular J-2 through a suitable incision to a position where end 32a of the guide wire moves into close proximity with the duct opening TD. With the expander assembly 33 retracted within the central lumen 40a of tubular member 40 in the manner shown in FIG. 3, the assemblage thus formed is carefully moved along the jugular vein J-2 being closely guided as it moves by the guide wire 32. When end 24a of tubular member 24 reaches the approximate position shown in FIG. 7, inner tubular member 40 is extended to permit the expander means to expand outwardly in the manner shown in FIG. 7, with the skirt means surrounding the duct opening. In the preferred form of the invention, the skirt portion of the flexible sheath is covered with a suitable, biocompatible adhesive material such as glycerol, lecithin, or hydrogel, gum, chitin, or other biocompatible wet adhesive compound or the like, adapted to removably wet tack the skirt portion 38a securely about the duct opening so as to positively enclose the ductile openings designated as "DO" in FIG. 7. Catheter location can be confirmed using cystoscopy, fluoroscopy, or other imaging techniques.

With the apparatus positioned in the manner illustrated in FIG. 7, the catheter is fixed at the incision with a standard IV catheter wing clamp and dressing. The drainage port 49 is then connected in a sterile manner to a lymph collection device for controlled removal of lymph fluid.

Turning now to FIGS. 8–11 a second embodiment of the access device of the present invention is there illustrated. This embodiment of the invention comprises an elongated tubular member 50 having first and second ends 50a and 50b guide means associated with tubular member 50 for controllably orienting first end 50a thereof and lymph fluid collection means disposed proximate first end 50a of tubular member 50 for collecting lymph fluid from a location proximate the termination of a selected one of the thoracic duct and the lymphatic duct.

As best seen by referring to FIGS. 9, 10 and 11, tubular member 50 includes an axially extending first central passageway or lumen 52, a thickened wall portion 54 and a second passageway 56 extending the length of thickened wall portion 54. As indicated in FIG. 9 passageway 56 terminates in an outlet port 56a located proximate first end 50a of tubular member 50.

Forming an important feature of the embodiment of the invention shown in FIGS. 8 through 12 is inflation means disposed proximate the first end of elongated member 50 for movement between the deflated configuration to an inflated configuration for removably affixing the first end 50a of elongated tubular member 50 within a selected one of the thoracic duct or the right lymphatic duct.

In this second embodiment of the invention, the inflation means comprises an annular shaped balloon-like member 58 the inner walls of which are affixed as by bonding to tubular member 50 proximate first end 50a thereof. When member 58 is suitably affixed to the outer walls of member 50 an internal annular shaped cavity 60 is formed between the inner surfaces of member 58 and the outer surfaces of tubular member 50. Annular member 58 is strategically positioned around member 50a so that this internal cavity 60 is in communication with outlet port 56a of fluid passageway 56. With this construction when a suitable liquid or gas, such as water, air or an inert gas flows under pressure through passageway 56 the fluid will cause annular member, or balloon 58 to expand from its first deflated configuration into its second inflated configuration as indicated by the phantom lines in FIG. 9. Referring particularly to FIG. 12 it is to be noted that when the device is properly located within either the thoracic duct or the right lymphatic duct movement of inflation member 58 into its second expanded position will cause its outer surfaces to pressurally engage the side walls of the duct and securely position the apparatus within the duct opening in the manner shown in FIG. 12.

Referring once again to FIG. 8 provided proximate end 50b of tubular member 50 is a generally Y-shaped assemblage 62 having a body portion 62a one end of which is closely receivable over end 50b of tubular member 50. Provided at the other end of body portion 62a is an opening 64 adapted to closely receive the guide means of this embodiment of the invention. Extending angularly outwardly from body portion 62a of the Y-shaped assemblage is a tubular segment 62b which terminates at its outboard end in a connector assemblage 66 for interconnection therewith of a drainage tube 68 for use in draining lymphatic fluids through lumen 52 of member 50.

As illustrated in FIG. 8, end 50a of tubular member 50 is curved like a stent to facilitate tip location and orientation of the device into the lymph duct. As was the case with the earlier form of the invention described herein, the entire catheter is radio-opaque, or alternatively a stripe along the length of the catheter is radio-opaque, to facilitate the use of fluoroscopy to confirm catheter location and orientation. The guide means of the present form of the invention is provided in the form of a guide wire or stylus 70 which is slidably receivable within central lumen or passageway 52 of tubular member 50. As best seen by referring to FIG. 11 stylus 70, when inserted within central passageway of member 50, will cause the curved end portion 50a of the tubular member to be straightened in the manner shown in FIG. 11. It is apparent that by selectively positioning the enlarged head portion 70a of the stylus 70 along the length of the curved portion member 50, various degrees of curvature of the member can be achieved so as to enable precise positioning of the device within the duct in the manner shown in FIG. 12. When the device is in the desired position within the opening of the duct and the inflation means or balloon member 58 is inflated, the stylus can be removed from the apparatus in the direction of the arrow of FIG. 12.

In using the apparatus of the invention shown in FIGS. 8 through 12, upon confirmation of the opening of the lymphatic duct to be accessed, the apparatus is inserted into either the subclavian or internal jugular vein within approximately 20 centimeters from the duct. The tip of the apparatus is oriented so as to guide the device up to and into the duct using fluoroscopy, optical cystoscopy or other imaging techniques. The tip of the apparatus is oriented by advancing or retracting the stylus 70 in the central lumen of member 50. Once oriented the inflation means or catheter balloon 58 is gently inflated inside the duct just ahead of the junction and the proximal end of the catheter is fixed at he incision site with a standard IV catheter wing clamp and dressing. The drainage lumen of the apparatus is then connected in a sterile manner to a lymph collection device which includes drainage member 68. Drainage of the lymph fluid occurs through access openings 72 provided proximate end 50a of member 50.

Figure 13:
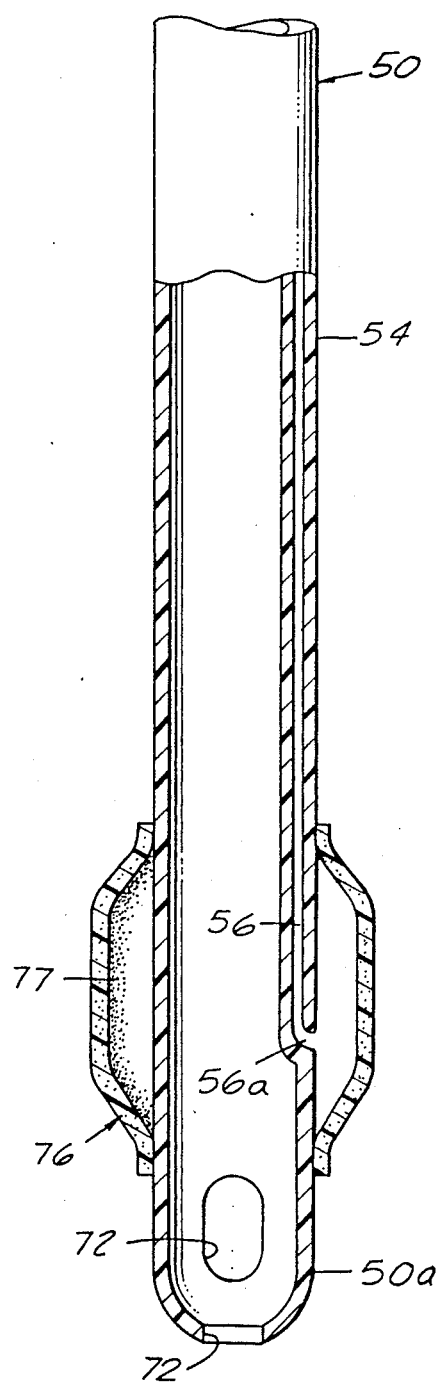
FIG. 13 is a fragmentary view, partly in cross-section of the distal end of an alternate form of balloon type catheter of the invention having a differently configured balloon tip.
Figure 14:
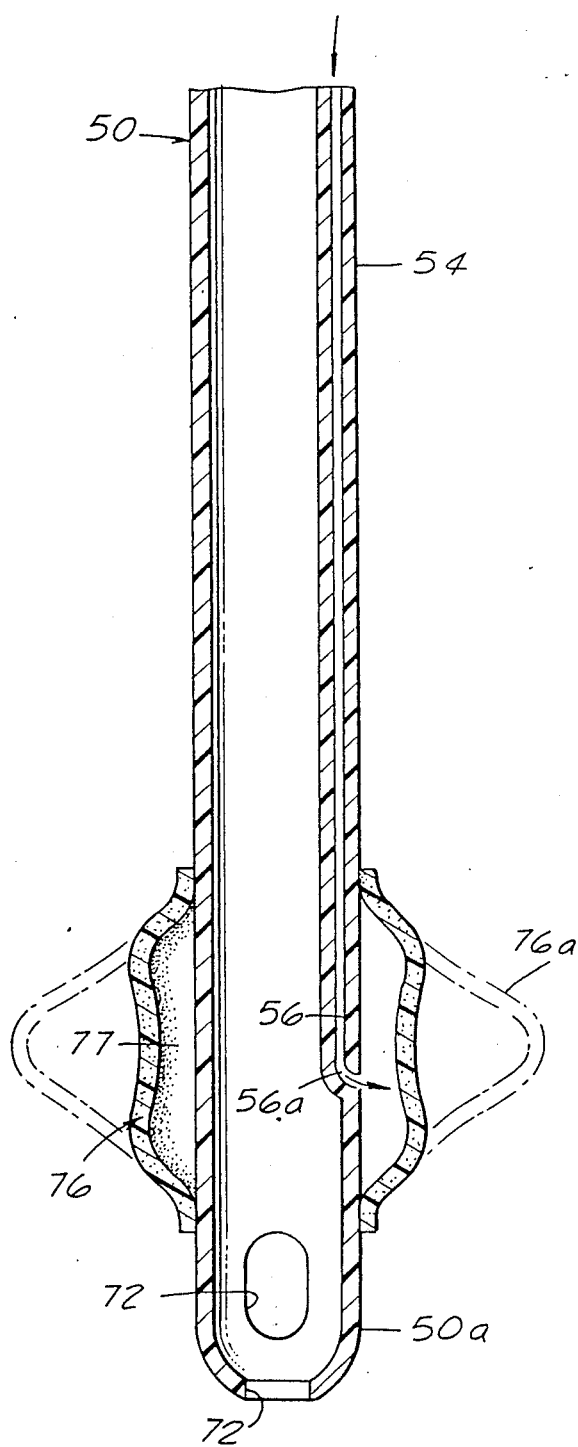
FIG. 14 is a fragmentary view, partly in cross-section of the device shown in FIG. 13 illustrating in phantom lines the appearance of balloon tip in an expanded configuration.

Turning now to FIG. 13 and 14, another alternate form of the apparatus of the invention is there illustrated. This form of the apparatus is similar in many respects to the apparatus illustrated in FIGS. 8 through 12 and like numerals are used to identify like components. This further alternate form of the invention also includes an elongated tubular member 50 having first and second ends 50a and 50b. Member 50 of this form of the invention is identical in construction to member 50 of the previously described invention having a thickened wall portion 54 through which a fluid passageway 56 is provided. This latter form of the invention also includes guide means associated with tubular member 50 for controllably orienting first end 50a of the apparatus within either the thoracic duct or the right lymphatic duct. The device further includes lymph fluid collection means disposed proximate the first end of the tubular member for collecting lymph fluid from a location proximate the termination of either the thoracic duct and the right lymphatic duct.

An important feature of the embodiment of the invention shown in FIGS. 13 and 14 resides in the design of the inflation means which is located proximate first end 50a of member 50 for movement between a deflated configuration as shown in FIG. 13 into an inflated configuration as illustrated by phantom lines in FIG. 14. The inflation means is here provided in the form of a balloon-like inflation member 76 which like member 58 is inflatable by a fluid such as liquid or gas flowing into the interior of the inflatable member via passageway 56a. In this embodiment of the invention the inflatable member 76 is somewhat elongated having a substantially distendable central portion 76a which upon introduction of fluid into chamber 77 will cause the central portion 76a to distend further outwardly than was the case with the balloon catheter 58 as described in connection with the previous embodiment of the invention.

This enables the apparatus illustrated in FIGS. 13 and 14 to be used in connection with thoracic or right lymphatic ducts whose opening are larger than that shown in FIG. 12 of the drawings.

The apparatus of the invention shown in FIGS. 13 and 14 is operated in the same manner as the apparatus shown in FIGS. 8 through 12 and the discussion of the operation of this last form of the invention will not be repeated here.

Having now described the invention in detail in accordance with the requirements of the patent statute, those skilled in this art will have no difficulty in making changes and modifications in the individual parts or their relative assembly in order to meet the specific requirements or conditions. Such changes and modifications may be made without departing from the scope and spirit of the invention as set forth in the following claims.

I claim:

1. A device for accessing a selected one of the thoracic duct and the right lymphatic duct to withdraw lymph fluid therefrom, comprising:
    (a) an elongated tubular member having first and second ends said tubular member having a lymph fluid drainage port located proximate said second end;
    (b) guide means slidably receivable within said tubular member for controllably orienting said first end thereof; and
    (c) lymph fluid collection and flow directing means slidably receivable within and disposed proximate said first end of said tubular member for collecting lymph fluid from a location proximate the termination of one of the thoracic duct and the right lymphatic duct and for directing the flow of the lymph fluid toward said fluid drainage port.

2. A device as defined in claim 1 in which said elongated tubular member includes an axially extending first central passageway and an enlarged wall portion having a second passageway extending the length thereof.

3. A device as defined in claim 2 in which said guide means comprises an elongated wire having a straight distal portion and a curved proximal portion, said wire being slidably receivable within said second passageway formed in said enlarged wall portion of said elongated tubular member.

4. A device as defined in claim 2 in which said collection means further comprises a second elongated tubular member slidably receivable within said central passageway of said tubular member, said second elongated tubular member having first and second ends.

5. A device as defined in claim 4 in which said lymph fluid collection means comprises an expander means disposed proximate said first end of said elongated inner tubular member for fixation around ductile openings disposed at the termination of a selected one of the thoracic duct and the right lymphatic duct.

6. A device as defined in claim 5 in which said expander means comprises an expanding assembly movable between a first contracted position when said expander assembly is disposed interiorly of said central passageway of said outer tubular member and a second expanded position when said expander assembly is disposed exteriorly of said central passageway of said outer tubular member.

7. A device as claimed in claim 6 in which said expander assembly comprises:

(a) a plurality of yieldably deformable tangs, each said tang having an outer end and an inner end connected to said first end of said elongated inner tubular member; and (b) a flexible sheath surrounding said tangs, said sheath terminating in a circumferentially extending skirt portion.

8. A device as defined in claim 2 in which said first end of said elongated tubular member is curved.

9. A device as defined in claim 8 further including inflation means disposed proximate said first end of said elongated member for movement between a deflated configuration to an inflated configuration for removably affixing said first end of said elongated tubular member within one of said thoracic duct and said right lymphatic duct.

10. A device as defined in claim 9 in which said inflatable means comprises an annular shaped member affixed to said elongated tubular member, said annular member having an internal cavity and being constructed of a yieldably, deformable elastomeric material expandable by a fluid medium from said first deflated configuration to said second inflated configuration.

11. A device as defined in claim 10 in which said annular shaped member circumscribes said first end of said second passageway provided in said enlarged wall portion of said elongated tubular member, said second passageway being adapted to carry fluid toward and away from said internal cavity of said annular shaped member.

12. A device for selectively accessing the veins disposed at one of the termination of the thoracic duct and the right lymphatic duct, comprising:

(a) An elongated outer tubular member having first and second ends and including a wall portion and an axially extending first central passageway, said wall portion having a second passageway extending the length thereof;

(b) guide means receivable said second passageway for guiding the path of travel of said first end of said outer tubular member;

(c) an elongated inner tubular member having first and second ends, said inner tubular member being slidably receivable within said axially extending first central passageway of said elongated outer tubular member; and (d) lymph fluid collection means connected to said inner tubular member proximate said first end thereof for surrounding the veins disposed at the termination of one of the thoracic duct and the right lymphatic duct.

13. A device as defined in claim 12 in which said guide means comprises an elongated wire having a curved end portion, said guide wire being slidably receivable within said second passageway.

14. A device as defined in claim 12 in which said lymph fluid collection means comprises an expander movable between a first contracted position when said expander is disposed interiorly of said central passageway of said outer tubular member and a second expanded position when said expander is disposed exteriorly of said central passageway of said outer tubular member.

15. A device as defined in claim 14 in which said expander comprises:

(a) a plurality of yieldably deformable tangs, each said tang having an outer end and an inner end connected to said distal end of said elongated inner tubular member; and (b) a flexible sheath surrounding said tangs, said sheath terminating in a circumferentially extending skirt portion.

16. A device as defined in claim 15 in which said skirt portion of said flexible sheath is covered with an adhesive material adapted to removably affix said skirt portion about the veins disposed at the termination of the thoracic duct and the lymphatic duct.

17. A method for accessing a selected one of the thoracic duct and the right lymphatic duct to remove lymph fluid therefrom using a catheter of the character having at least two lumens; a fluid inlet tip portion in communication with one of said lumens; guide means receivable within one of said lumens for controllable positions the fluid inlet tip portion thereof; and lymph fluid collection means disposed proximate the fluid inlet tip portion for collecting the lymph fluid, said method comprising the steps of:

(a) inserting the catheter into selected one of the subclavian vein and internal jugular vein;

(b) using said guide means and appropriate imaging techniques, positioning said inlet tip portion of the catheter at a location proximate the selected said duct opening;

(c) removably affixing said inlet tip portion of the catheter proximate to the duct opening; and (d) controllably removing lymph fluid from the duct.

18. A method as defined in claim 17 in which the duct to be accessed terminates in many small vessels and in which the inlet tip portion of the catheter is removably affixed to the duct opening by means of a wet tack adhesive.

19. A method as defined in claim 17 in which the duct to be accessed terminates in a single vessel; in which said fluid inlet tip portion of the catheter includes a balloon member having an internal cavity expandable by fluid pressure; and in which said fluid inlet tip portion of the catheter is removably affixed to the duct opening by the further step of inserting fluid under pressure into said internal cavity of said balloon member to cause said balloon member to pressurally engage the inner walls of the duct to hold the apparatus securely in position.

20. A device for accessing a selected one of the thoracic duct and the right lymphatic duct, comprising:

(a) an elongated tubular member having first and second ends:

(b) guide means slidably receivable within said tubular member for controllably orienting said first end thereof; and (c) lymph fluid collection means slidably receivable within and disposed proximate said first end of said tubular member for collecting lymph fluid from a location proximate the termination of one of the thoracic duct and the right lymphatic duct, said collection means comprising:

(i) a second elongated tubular member slidably receivable within said tubular member, said second elongated tubular member having first and second ends; and (ii) an expander means connected proximate said first end of said elongated inner tubular member for fixation around ductile openings disposed at the termination of a selected one of the thoracic duct and the right lymphatic duct.

* * * * *